United States Patent [19]

Kiske et al.

[11] Patent Number: 4,924,861
[45] Date of Patent: May 15, 1990

[54] PISTON AND CYLINDER UNIT AS SUPPLY DEVICE FOR THE RESPIRATORY AIR OF A RESPIRATOR

[75] Inventors: Siegfried Kiske, Gross Gronau; Erik Schwanbom; Carl F. Wallroth, both of Lubeck, all of Fed. Rep. of Germany

[73] Assignee: Drägerwerk AG, Lübeck, Fed. Rep. of Germany

[21] Appl. No.: 366,470

[22] Filed: Apr. 12, 1989

[30] Foreign Application Priority Data

May 19, 1988 [DE] Fed. Rep. of Germany ....... 3817091

[51] Int. Cl.⁵ .............................................. A62B 23/02
[52] U.S. Cl. .................................................. 128/205.18
[58] Field of Search ...................... 128/204.18, 204.21, 128/204.26, 204.27, 204.29, 205.15, 205.18

[56] References Cited

U.S. PATENT DOCUMENTS

| 2,711,169 | 6/1955 | Hull et al. | 128/204.29 |
|---|---|---|---|
| 3,358,680 | 12/1967 | Chabanier | 128/204.29 |
| 3,425,409 | 2/1969 | Isaacson et al. | 128/205.18 |
| 3,651,804 | 3/1972 | Spiller | 128/205.18 |
| 3,749,524 | 7/1973 | Jordan | 128/205.18 |
| 4,340,044 | 7/1982 | Levy | 128/205.15 |
| 4,472,082 | 9/1984 | Kroling | 128/205.18 |
| 4,782,831 | 11/1988 | Gallant | 128/204.18 |
| 4,836,198 | 6/1989 | Gates | 128/205.18 |

FOREIGN PATENT DOCUMENTS

| 429812 | 1/1975 | U.S.S.R. | 128/204.27 |
|---|---|---|---|
| 834152 | 5/1960 | United Kingdom | 128/205.15 |
| 1078247 | 9/1967 | United Kingdom | 128/205.15 |

Primary Examiner—Eugene H. Eickholt
Attorney, Agent, or Firm—McGlew & Tuttle

[57] ABSTRACT

A piston and cylinder unit provides a supply actuable by means of an actuation device for delivering respiratory air in a respiratory cycle of a respirator. Its piston is sealed with its cylinder by means of a pair of rolling membranes arranged symmetrically with regard to one another. The membranes separate the cylinder contents into an antechamber and a working chamber. The wear of the rolling membranes during the working strokes and especially during the starting is decreased by a clean rolling of the folds. Also a leakage control takes place even during operation and an immediate detection of leaks due to bending stress, aging or other influences is guaranteed. For this purpose an inner chamber which is enclosed by the two rolling membranes is under a pressure different from the pressure in the antechamber and the working chamber so that the highest pressure is on a concave inside of the folds.

8 Claims, 2 Drawing Sheets

PISTON AND CYLINDER UNIT AS SUPPLY DEVICE FOR THE RESPIRATORY AIR OF A RESPIRATOR

FIELD AND BACKGROUND OF THE INVENTION

The invention relates in general to respirators and in particular to a new and useful piston-cylinder unit employed as a respiratory gas supply unit which can be actuated by means of an actuation device for the respiratory gas in the respiratory cycle of the respirator.

Actuation units in various executions are used for the transport of the respiratory gas in the respiratory cycle of a respirator, a well-known kind of actuation device is described in the monograph: "Automatic Ventilation of the Lungs", William W. Mushin et al., Blackwell Scientific Publications, 3rd edition, pages 273 to 277. Herein the diagram of a respirator is shown in which the respiratory air is transported in the respiratory cycle by means of a piston-cylinder unit. The outer surface of the piston is sealed off against the inner wall of the cylinder by means of two rolling membranes which can follow the piston movement in both directions in their fold arranged between the piston and the cylinder. The rolling membranes separate the cylinder chamber into a working chamber for the generation of the pressure required for the artificial respiration and an antechamber in which the air is taken in during the working stroke to generate a vacuum during the expiration. The actuation device is an electro-motor with a gear and levers for the transmission of the rotating movement into a lifting movement. During the artificial respiration the piston executes alternating stroke movements for the generation of inspiration-phases and expiration-phases, whose frequency and lift of stroke can be varied by means of a gear and lifting rod. Therefore, depending on the control of the piston, the rolling membranes execute a shorter or longer lift of stroke, during which the respective fold of the rolling membrane rolls off in the space between the piston and the inner surface of the cylinder, following the lift of the stroke.

In an arrangement of the rolling membrane according to the known piston-cylinder unit it is disadvantageous, that because of the changing pressure conditions in the antechamber as well as in the working chamber the capability of the membrane material to roll off becomes irregular and unpredictable in the proximity of the fold and may even fail when the membrane material sticks to itself in the fold. This danger is given particularly during the starting of the piston, as no respiratory pressure has built up yet. Such an unnoticed wear easily leads to leaks in the material, and therefore to pressure loss and gas loss. This can have serious consequences in nowadays precisely dosed amounts of gas in respiration methods with less and less gas surplus and a respiratory cycle which is practically a closed cycle.

SUMMARY OF THE INVENTION

The invention provides a cylinder unit in which the wear of the rolling membranes is decreased during the working strokes and during the starting in particular, due to a clean rolling off of the folds. Also, a leak control during operation becomes possible as well as an immediate detection of leaks due to bending stress, aging or other reasons.

The pressure supply for the inner chamber enclosed by the two rolling membranes between the piston and the cylinder guarantees that the fold keeps its shape and that it lies close smoothly to the walls of the piston and the cylinder, thus allowing their movements to be free of friction and wear. As the rolling membrane rolls off over the whole circumference of the piston, one-sided stress is avoided. By controlling the pressure in the inner chamber a leak can be detected easily and immediately during operation.

If the convex outsides of the folds face one another, the inner chamber enclosed by them is kept in a vacuum. If, however, the concave insides of the folds face one another, the inner chamber has to be kept under pressure.

The pressure in the inner chamber stabilizes the material surfaces of the rolling membranes, which make an exact axial lift of stroke possible. Thus it has become possible to determine the lift of stroke of the piston by means of a displacement transducer. A reference between the travel of the piston and the respiratory air volume supplied can be established easily. As now the walls of the rolling membranes no longer give way under the pressure in the antechamber or the working chamber, which differs from the pressure in the inner chamber, the conversion from lift of stroke to stroke volume has such a small range of error, that now even small respiratory air volumes can be dosed by means of a piston-cylinder unit.

Advantageously the inner chamber enclosed by the rolling membranes is connected to a pressure supply unit and to a pressure meter registering the inner pressure. By this means the internal pressure can be set depending on the operation conditions and the requirements, and the pressure in the inner chamber can be controlled. Leak controls can be made anytime during the operation of the piston-cylinder unit, and possibly occurring leaks due to bending stress, aging or other influences can be detected immediately.

It is advantageous to connect the pressure meter to the supply unit by means of a signal line, so that the actual value measured can be compared to the set pressure value storable in the supply unit. By this means even variable pressure values for the inner chamber can be controlled.

If the actual pressure value and the set pressure value do not coincide, it is advantageous to deactivate the actuation device by means of a control unit and thus avoid a further misoperation of the piston-cylinder unit. By means of additional warning signals during such improper working conditions the mistake can be eliminated immediately by the personnel operating the device.

Accordingly it is an object of the invention to provide a piston and cylinder unit for supplying respiratory gas to a patient and which comprises a cylinder which has a cylinder side wall with a delivery end and a delivery supply connection and an opposite base plate end providing a bearing mounting for a piston rod of the piston which is movable in the cylinder and which includes a pair of rolling membranes which have cylinder engagement ends engaged with the cylinder wall at spaced opposed locations along its length and opposite piston engagement ends engaged with the side wall of the piston at spaced apart opposed locations and which define an enclosed pressure antechamber between the rolling membranes and between the piston and the cylinder and which includes an arrangement for maintaining the pressure in the space between the membranes above that of the working pressure of the cylinder as the piston rod is moved backwardly and forwardly to move the piston in a pumping operation.

A further object of the invention is to provide a pumping device particularly for respirators which is simple in design, rugged in construction and economical to manufacture.

The various features of novelty which characterize the invention ar pointed out with particularity in the claims annexed to and forming a part of this disclosure. For a better understanding of the invention, its operating advantages and specific objects obtained by its uses, reference is made to the accompanying drawing and descriptive matter in which preferred embodiments of the invention are illustrated.

DETAILED DESCRIPTION OF PREFERRED EMBODIMENTS

Figure 1:
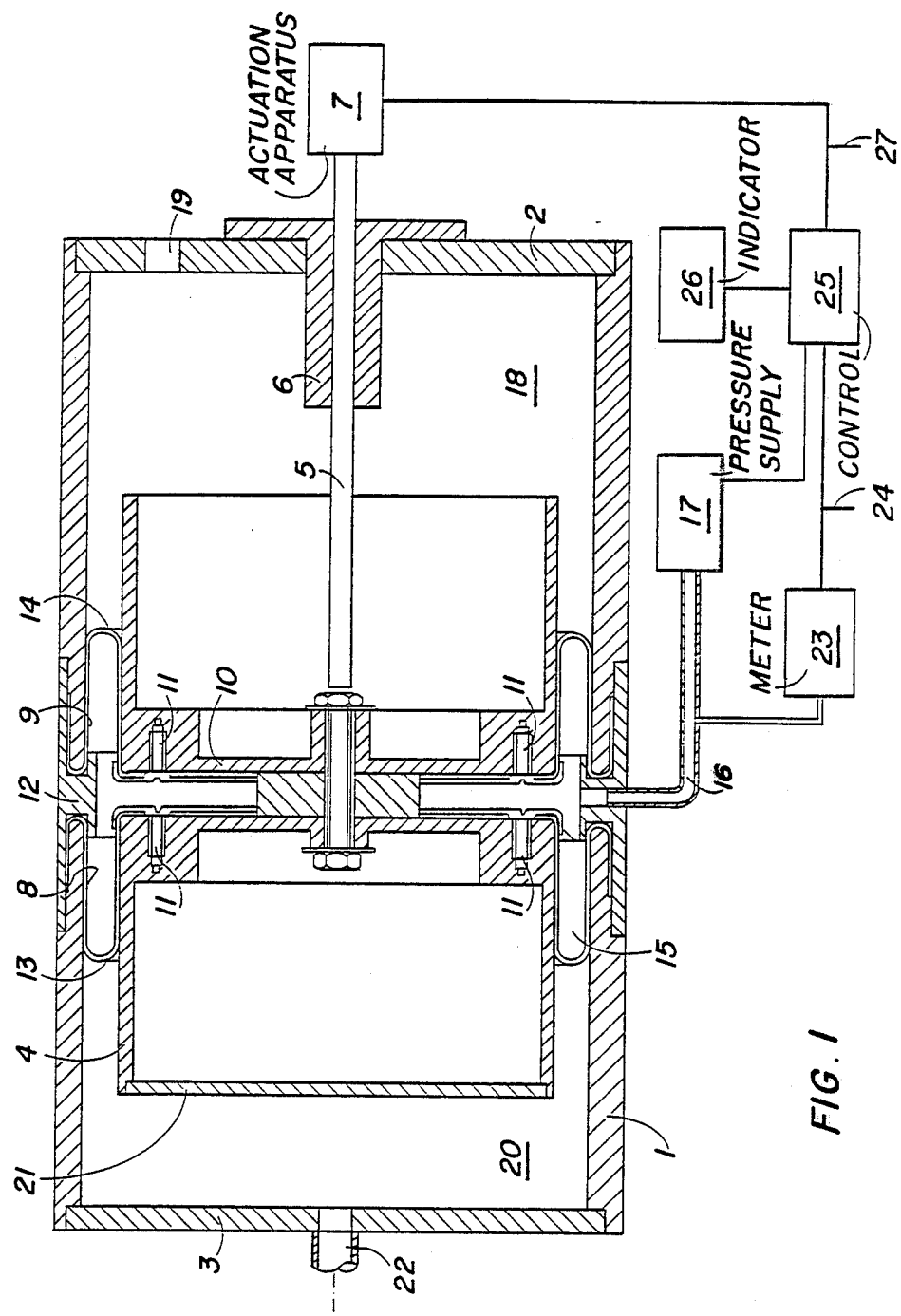
FIG. 1 is an axial sectional view of a respirator pumping device constructed in accordance with the invention.

As shown in the drawings, a cylinder 1 is represented whose end faces are closed by means of a base plate 2 and an end plate 3. A piston 4 on a piston rod 5 is guided in an axial bearing 6 and is received in the interior of the cylinder 1. The piston rod 5 is connected to an actuation means 7.

Figure 2:
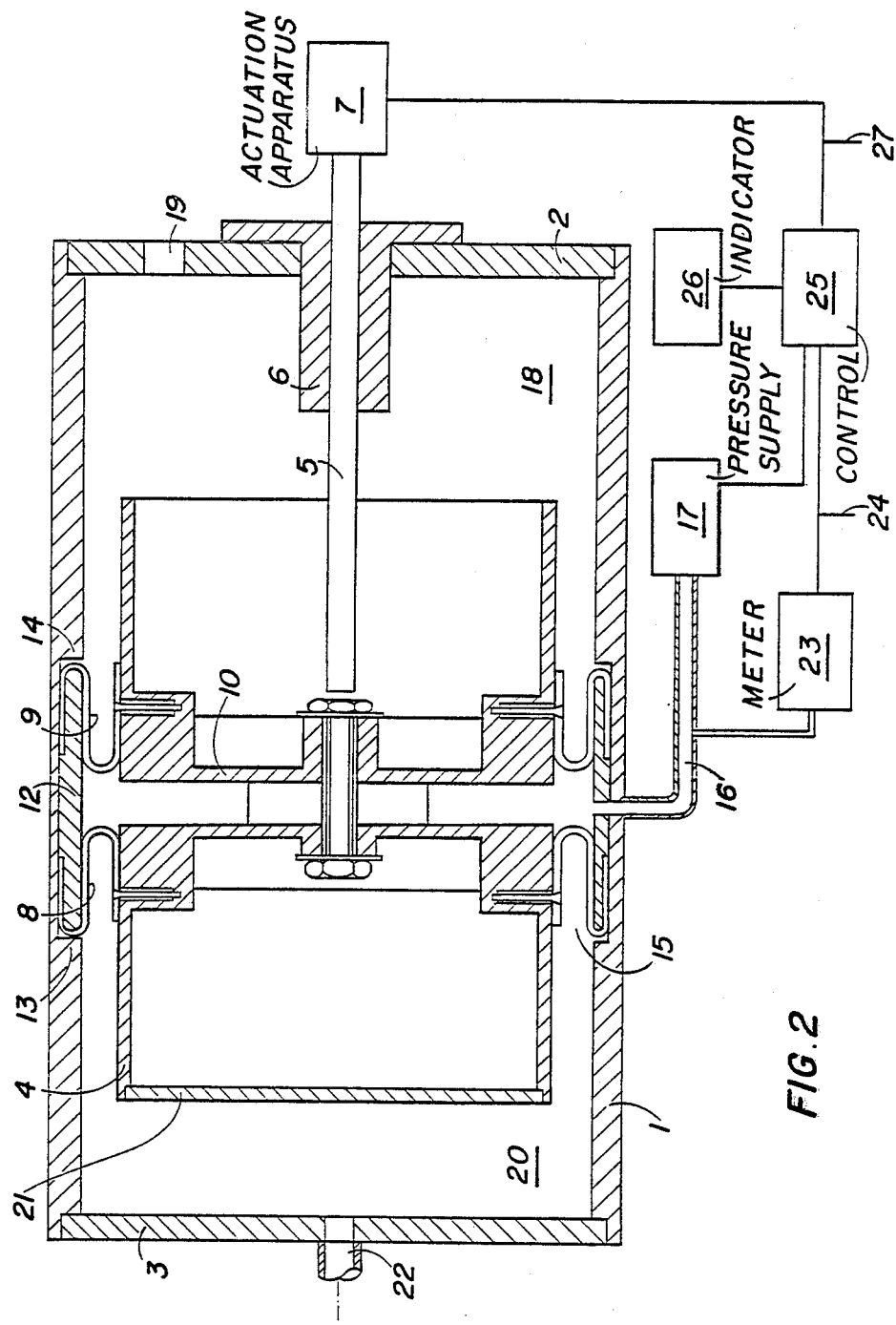
FIG. 2 is an axial sectional view of another embodiment of a respirator pumping device constructed in accordance with the invention.

The outer surface of the piston 4 is sealed off against the cylinder by means of a double rolling membrane or rolling twin membrane 8 and 9, which is fastened by means of screws 11 on an intermediate floor running radially inside the piston 4 and also clamped in the cylinder 1 by means of a clamping connection 12. In FIG. 1, the concave insides of the folds 13 and 14 face one another. In FIG. 2 the convex sides of the folds 13 and 14 face one another. Inner chambers 15 enclosed by the membranes 8 and 9 are kept under pressure by a pressure line 16 by means of a pressure supply unit 17. The membranes 8 and 9 separate the inner chamber of the cylinder 1 into an antechamber 18 which is connected to the environment by means of an opening 19 and a working chamber 20, which has a working pressure generated by the strokes of the piston 4. On the face of the piston located in the working chamber the piston has a face plate 21. The respiratory air displaced during the working stroke can be transported to the respiratory circle of a respirator (not shown) through a connection muff or conduit 22 arranged on the connection plate 3. A pressure meter 23 is connected to the pressure line 16, whose measuring signals are passed on to the control unit 25 by means of a signal line 24. The control unit 25 also registers the set pressure value entered into the pressure supply unit 17. An indicator unit 26 shows the actual conditions and gives warning signals if necessary. In the event of improper working conditions, such as can be the result of an undesired deviation of the actual pressure value from set value, the actuation device 7 can be deactivated by means of a respective signal of the control unit 25 through the control line 27.

While specific embodiments of the invention have been shown and described in detail to illustrate the application of the principles of the invention, it will be understood that the invention may be embodied otherwise without departing from such principles.

What is claimed is:

1. A piston and cylinder unit for supplying respiratory gas to a patient, comprising a cylinder having a cylindrical side wall, a delivery end with a delivery supply connection and an opposite base plate end, a piston movable in said cylinder and having a piston side wall, a piston rod journalled in said base plate end and connected to said piston, a pair of rolling membranes having cylinder engagement ends engaged with said cylinder side wall at spaced opposed locations, said membranes having an end opposite said cylinder engagement ends engaged with said side wall of said piston at spaced opposed locations on said piston and defining an enclosed pressure inner chamber between said rolling membranes and between said piston and said cylinder said rolling membranes having a concave side and an opposite convex side, said rolling membranes separating said cylinder into an antechamber and a working chamber leading to said delivery supply connection, and means connected to said inner chamber to maintain a pressure in said inner chamber keeping said concave side at a pressure which is higher than said convex side.

2. A piston and cylinder unit according to claim 1, wherein said pair of rolling membranes are arranged symmetrically with regard to one another, the pressure in said inner chamber between said rolling membranes being acted upon from one side by said working chamber on said antechamber and on the opposite side by the pressure delivered to said inner chamber so that the highest pressure is on the concave inside of the folds of said rolling membranes, said inner chamber being kept in a vacuum with regard to the chambers between the delivery end of said cylinder and said piston and between the opposite base end and said piston, said rolling membranes having intermediate portions which have convex outsides which face one another.

3. A piston and cylinder unit according to claim 1, wherein the pressure maintained in said inner chamber is greater than the pressure in said working chamber and said antechamber, and said concave sides of said rolling membranes face each other.

4. A piston and cylinder unit for supplying respiratory gas to a patient, comprising a cylinder having a cylindrical side wall with a delivery end having a delivery supply connection and an opposite base plate end, a piston movable in said cylinder and having a piston side wall, a piston rod journalled in said base plate end connected to said piston, a pair of rolling membranes having cylinder engagement ends engaged with said cylinder wall at spaced opposed locations and having opposite piston engagement ends engaged with said side walls of said piston at spaced apart opposed locations and defining an enclosed pressure chamber between said rolling membranes and between said piston and said cylinder and separating said cylinder into an antechamber between said piston and said base plate end and a working chamber between said piston and said delivery end, means connected to said pressure chamber to maintain a pressure which is different from the working pressure of said cylinder, and means connected to said piston rod to move said rod with said piston through working strokes to deliver respiratory gas through said delivery supply connection, said means connected to said piston rod including a displacement transducer for determining the path of movement of said piston.

5. A piston and cylinder unit according to claim 4, wherein said pressure chamber enclosed by said rolling membranes is connected to a pressure supply unit and to a pressure meter registering the internal pressure between said rolling membranes.

6. A piston and cylinder unit according to claim 5, including control means connected into said pressure chamber, said control means including a pressure meter, a control unit connected to said pressure meter through a signal line and reading measured actual pressure values for comparison with a value which can be stored in said supply unit.

7. A piston and cylinder unit according to claim 4, wherein said means connected to said piston comprises an actuation device which can be activated, a control unit connected to said actuation device and connected to the pressure chamber between said rolling membranes for actuating said control unit.

8. A piston and cylinder unit according to claim 4, wherein said piston includes separable half portions which are connected together over said opposite piston engagement ends of said rolling members, said cylinder having a side wall with separatable parts which are brought together over portions of said cylinder engagement ends of said rolling membranes.

* * * * *